United States Patent
Tardif et al.

(10) Patent No.: US 11,844,771 B2
(45) Date of Patent: Dec. 19, 2023

(54) METHODS OF TREATING ACUTE RESPIRATORY DISTRESS SYNDROME USING COLCHICINE

(71) Applicant: INSTITUT DE CARDIOLOGIE DE MONTREAL, Montreal (CA)

(72) Inventors: Jean-Claude Tardif, Montreal (CA); Jocelyn Dupuis, Montreal (CA)

(73) Assignee: INSTITUT DE CARDIOLOGIE DE MONTREAL, Montreal (CA)

( * ) Notice: Subject to any disclaimer, the term of this patent is extended or adjusted under 35 U.S.C. 154(b) by 0 days.

(21) Appl. No.: 17/714,238

(22) Filed: Apr. 6, 2022

(65) Prior Publication Data

US 2022/0362181 A1    Nov. 17, 2022

Related U.S. Application Data

(60) Provisional application No. 63/171,170, filed on Apr. 6, 2021.

(51) Int. Cl.
*A61K 31/165* (2006.01)
*A61P 11/00* (2006.01)
*A61K 9/00* (2006.01)

(52) U.S. Cl.
CPC .......... *A61K 31/165* (2013.01); *A61K 9/0053* (2013.01); *A61P 11/00* (2018.01)

(58) Field of Classification Search
CPC .................................................. A61K 31/165
See application file for complete search history.

(56) References Cited

FOREIGN PATENT DOCUMENTS

WO    WO-2021/184128 A1    9/2021

OTHER PUBLICATIONS

Dupuis et al., PLOS ONE, 2020, 15(12): e0242318.*
Manuel et al., Eur Respir J., 2020, 56: 1-12.*
Matthay et al. Nature Review, 2019, 5:18, pp. 1-22.*
Bellani et al., "Epidemiology, Patterns of Care, and Mortality for Patients With Acute Respiratory Distress Syndrome in Intensive Care Units in 50 Countries," JAMA. 315(8):788-800 (2016).
Channappanavar et al., "Pathogenic human coronavirus infections: causes and consequences of cytokine storm and immunopathology," Semin Immunopathol. 39(5):529-539 (2017).
Chen et al., "Glibenclamide alleviates inflammation in oleic acid model of acute lung injury through NLRP3 inflammasome signaling pathway," Drug Des Devel Ther. 13:1545-1554 (2019).
Chen et al., "Severe Acute Respiratory Syndrome Coronavirus Viroporin 3a Activates the NLRP3 Inflammasome," Front Microbiol. 10:50 (2019) (9 pages).
Dupuis et al., "Colchicine reduces lung injury in experimental acute respiratory distress syndrome," PLoS One. 15(12):e0242318 (2020) (15 pages).
Fan et al., "Acute Respiratory Distress Syndrome: Advances in Diagnosis and Treatment," JAMA. 319(7):698-710 (2018).
Herold et al., "Acute lung injury: how macrophages orchestrate resolution of inflammation and tissue repair," Front Immunol. 2:65 (13 pages) (2011).
Kumar et al., "Partners in crime: neutrophils and monocytes/macrophages in inflammation and disease," Cell Tissue Res. 371(3):551-565 (2018).
Martinez et al., "Colchicine Acutely Suppresses Local Cardiac Production of Inflammatory Cytokines in Patients With an Acute Coronary Syndrome," J Am Heart Assoc. 4(8):e002128 (2015) (10 pages).
Martinez et al., "The NLRP3 inflammasome and the emerging role of colchicine to inhibit atherosclerosis-associated inflammation," Atherosclerosis. 269:262-271 (2018).
Otani et al., "Colchicine prevents NSAID-induced small intestinal injury by inhibiting activation of the NLRP3 inflammasome," Sci Rep. 6:32587 (10 pages) (2016).
Potey et al., "Neutrophils in the initiation and resolution of acute pulmonary inflammation: understanding biological function and therapeutic potential," J Pathol. 247(5):672-685 (2019).
Safi et al., "Neutrophils contribute to vasculitis by increased release of neutrophil extracellular traps in Behçet's disease," J Dermatol Sci. 92(2):143-150 (2018).
Sweeney et al., "Acute respiratory distress syndrome," Lancet. 388(10058):2416-2430 (2016).
Tardif et al., "Efficacy and Safety of Low-Dose Colchicine after Myocardial Infarction," N Engl J Med. 381(26):2497-2505 (2019).
Thompson et al., "Acute Respiratory Distress Syndrome," N Engl J Med. 377(19):562-72 (2017).
Vaidya et al., "Colchicine inhibits neutrophil extracellular trap formation in acute coronary syndrome patients after percutaneous coronary intervention," medRxiv. Apr. 24, 2020 (37 pages).
Venet et al., "Lymphocytes in the development of lung inflammation: a role for regulatory CD4+ T cells in indirect pulmonary lung injury," J Immunol. 183(5):3472-80 (2009).
Wong et al., "Insights into the immuno-pathogenesis of acute respiratory distress syndrome," Ann Transl Med. 7(19):504 (2019) (10 pages).

\* cited by examiner

*Primary Examiner* — Rei Tsang Shiao
(74) *Attorney, Agent, or Firm* — Clark & Elbing LLP

(57) ABSTRACT

Disclosed are methods of treating Acute Respiratory Distress Syndrome using colchicine, e.g., by administering colchicine to a subject in need thereof.

20 Claims, 5 Drawing Sheets
(5 of 5 Drawing Sheet(s) Filed in Color)
Specification includes a Sequence Listing.

METHODS OF TREATING ACUTE RESPIRATORY DISTRESS SYNDROME USING COLCHICINE

SEQUENCE LISTING

The instant application contains a Sequence Listing which has been submitted electronically in ASCII format and is hereby incorporated by reference in its entirety. Said ASCII copy, created on Jul. 11, 2022 is named 50761-025002_Sequence_Listing_5_6_22_ST25 and is 12,227 bytes in size.

FIELD OF THE INVENTION

The invention relates to methods of treating acute respiratory distress syndrome (ARDS).

BACKGROUND

Acute Respiratory Distress Syndrome (ARDS) results from direct or indirect acute lung injury (ALI) leading to intense inflammation with alveolar edema producing respiratory failure. ARDS accounts for 10% of intensive care units admissions and for 24% of mechanically ventilated patients. In the United States alone, it affects approximately 200,000 patients per year with a high mortality rate ranging from 35% to 46%, with higher mortality being associated with greater initial ALI. Further, survivors of ARDS suffer from significant long-term morbidity affecting quality of life with physical, neuropsychiatric, and cognitive impairments. Besides oxygen and mechanical ventilatory support, there are no treatment options currently available and all trials with pharmacologic agents have shown neutral or even deleterious effects.

Colchicine is an inexpensive drug that is approved for acute use in patients with gout and chronic use in patients with Familial Mediterranean Fever.

There is a need for new therapies for treating ARDS that could reduce intensive care unit admissions, mechanical ventilation, and death rate, especially using readily available, inexpensive medications.

SUMMARY OF THE INVENTION

The invention provides a method of treating acute respiratory distress syndrome (ARDS) in a subject; the method including administering colchicine to the subject. In one embodiment, the subject has a coronavirus infection, e.g., a severe acute respiratory syndrome coronavirus 2 (SARS-CoV-2) infection.

In another embodiment, the subject has been diagnosed with COVID-19. In some embodiments, the subject has sepsis, pneumonia, severe trauma and tissue injury, inhaled harmful fumes or smoke, or inhaled vomited stomach contents from the mouth.

In some embodiments, the colchicine is administered daily, e.g., the colchicine is administered once, twice, or three times a day.

In other embodiments, the colchicine is administered twice daily for 3 days. In one embodiment, the colchicine is administered twice daily for 3 days followed by once daily. In another embodiment, the once daily administration is for 27 days.

In some embodiments, 0.3 to 2.4 mg, 0.3 to 1.8 mg, 0.4 to 0.6 mg, or 0.5 mg of colchicine is administered daily.

In one embodiment, the colchicine is in the form of a tablet. In another embodiment, the administration is oral administration.

In a further embodiment, the subject was diagnosed with ARDS within 24 hours prior to initiating the treatment.

In other embodiments, the administration of colchicine is initiated upon assessment in (a) an emergency department (ED), (b) a hospital, (c) a medical office setting, or (d) a coronavirus testing facility.

In some embodiments, treatment with colchicine reduces morbidity or mortality in the clinical course of ARDS, reduces symptoms caused by ARDS, or reduces the need for ventilator dependency.

In other embodiments, treatment with colchicine results in a decrease in one or more symptoms related to ARDS. In some embodiments, the one or more symptoms related to the ARDS is selected from a feeling that one cannot get enough air into the lungs, rapid breathing, low oxygen levels in the blood, and clicking, bubbling, or rattling sounds in the lungs when breathing.

In further embodiments, the colchicine is administered in combination with a second therapeutic. In some embodiments, the second therapeutic is an antiviral drug, an antimalarial drug, an anti-inflammatory drug, an antibiotic, an acid-reducing medicine, a blood thinner, a muscle relaxant, a pain reliever, a sedative, or a diuretic.

In other embodiments, the antiviral drug is remdesivir.

In further embodiments, the second therapeutic is an anti-inflammatory drug. In some embodiments, the anti-inflammatory drug is a steroid, parenteral immunoglobulin, or aspirin. In one embodiment, the steroid is dexamethasone.

In another embodiment, the second therapeutic is convalescent plasma from a subject who has recovered from a coronavirus infection.

In some embodiments, the subject is a human. In other embodiments, the subject is 1 to 5 years old, or the subject is less than one year old, or the subject is less than 21 years old, or the subject is 0 to 19 years old.

Definitions

The term "colchicine," as used herein, refers to a compound of the following structure:

The term "pharmaceutical composition," as used herein, represents a composition formulated with a pharmaceutically acceptable excipient, and manufactured or sold with the approval of a governmental regulatory agency as part of a therapeutic regimen for the treatment of disease in a subject.

The term "subject," as used herein, refers to a human suffering from or at risk ARDS. A subject may be diagnosed as having ARDS or may be one experiencing one or more symptoms of a coronavirus infection ARDS. Non-limiting examples of ARDS symptoms include a feeling that one cannot get enough air into the lungs, rapid breathing, low oxygen levels in the blood, and clicking, bubbling, or rattling sounds in the lungs when breathing. In some instances, the subject is a pediatric or adolescent subject, e.g., a subject that is less than 21 years old, 0 to 19 years old, 1 to 5 years old, or less than one year old.

"Treatment" and "treating," as used herein, refer to the medical management of a subject with the intent to improve, ameliorate, stabilize, prevent or cure a disease, disorder, or condition. This term includes active treatment (treatment directed to improve the disease, disorder, or condition); palliative treatment (treatment designed for the relief of symptoms of the disease, disorder, or condition); and supportive treatment (treatment employed to supplement another therapy). "Treatment" and "treating," as used herein, also refers to disease modification, meaning, that the expression of the disease is modified towards a less severe expression of the symptoms. For example, a treatment may reduce the lethal outcomes in the treated subjects relative to the untreated subjects, the need for mechanical ventilation for the treated subjects relative to the untreated subjects, or the viral load in the treated subjects relative to the untreated subjects.

The term "unit dosage form," as used herein, represents a unit of a pharmaceutical composition intended for administration to a subject as is without further modification. Non-limiting examples of a unit dosage form include a tablet, capsule, lozenge, wafer, film, sachet, and cachet. Preferably, the unit dosage form is a tablet.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
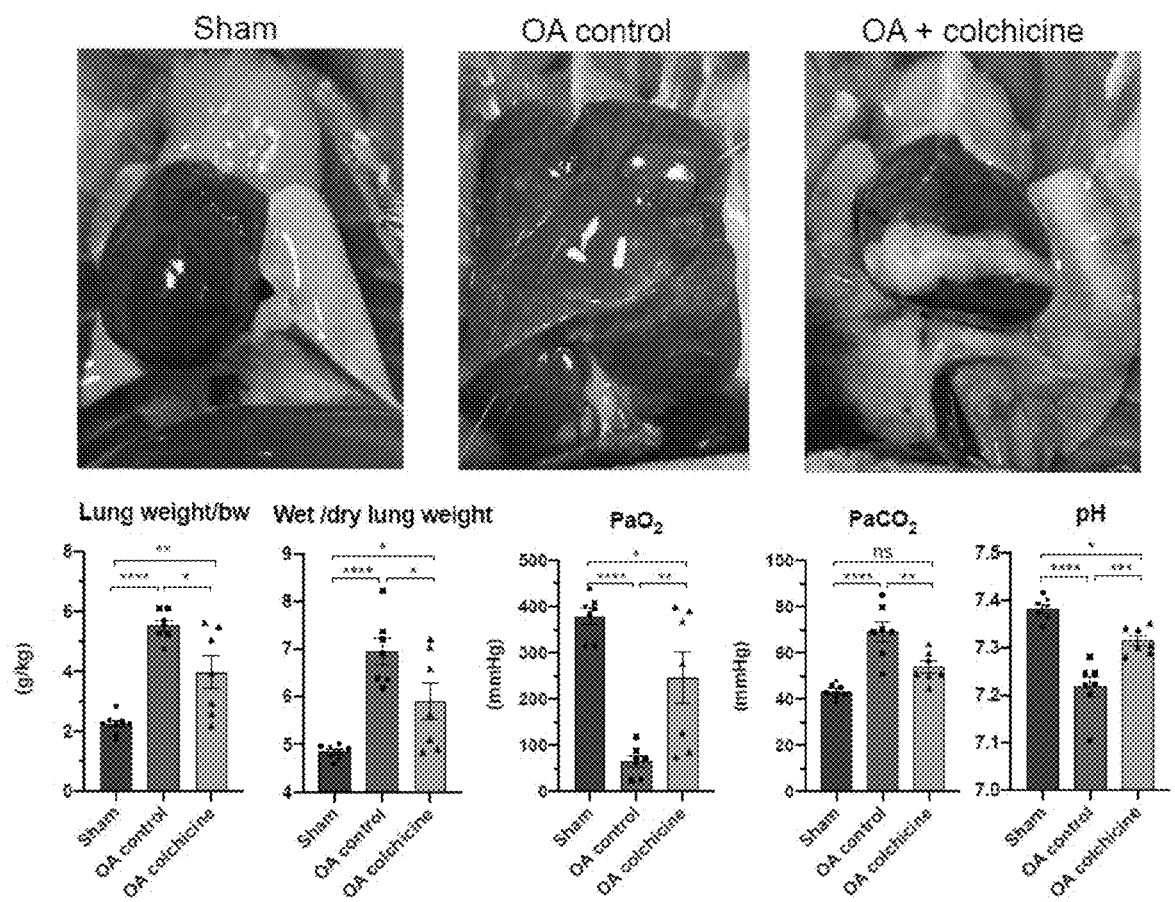
FIG. 1 is a series of images and graphs showing the effects of colchicine therapy on oleic acid-induced ALI, lung edema, and gas exchange. Shown are, left to right in the bar graphs, the control (Sham), oleic acid-induced ALI (OA control), and oleic acid induced ALI with colchicine (OA+colchicine). Values are mean±SEM. **$p<0.0001$; *$p<0.001$, **$p<0.01$; *$p<0.05$.

In general, the invention provides methods of treating ARDS in a subject using colchicine. The method typically involves administering colchicine to the subject in need thereof.

A rat model system was used to study the effects of colchicine pre-treatment on oleic acid-induced ARDS. In this model system, colchicine reduced histological lung injury by 61%, reduced lung edema, and markedly improved blood oxygenation by increasing $PaO_2/FiO_2$ from 66±13 mmHg (mean±SEM) to 246±45 mmHg. Lung neutrophil recruitment was reduced by colchicine with evidence for reduced neutrophils activation, as assessed by flow cytometry. The experimental results disclosed herein support the use of colchicine, a widely available low-cost drug, for the prevention of ARDS in conditions causing acute lung injury.

The early pathologic phase of ARDS, termed the "exudative" phase, is characterized by high-permeability alveolar edema with intense dysregulated inflammation. In this early phase following ALI, histological study reveals predominant neutrophilic alveolitis: activated polymorphonuclear neutrophils recruit to lung tissue in concert with monocytes and alveolar macrophages. It is recognized that neutrophils play a major role in lung tissue injury by their rapid recruitment and their release of proteases (myeloperoxidase (MPO), elastase, matrix metalloproteases (MMP), free oxygen radicals and neutrophils extracellular traps (NETs). Initial neutrophils recruitment results from the release of pathogen-associated molecular patterns (PAMPs) and damage-associated molecular patterns (DAMPs) activating the inflammasome. PAMPs include lipopolysaccharide (LPS), lipoteichoic acid, DNA, RNA and foreign proteins such as formylated peptides released by infectious agents and recognized by immune receptors such as Toll-like receptors.

DAMPs are released after tissue injury and include high mobility group box 1 (HMGB1), heat shock proteins, hyaluronan and mitochondrial-derived factors. While neutrophils play a critical role in ALI, macrophages and monocytes orchestrate resolution of inflammation and tissue repair, whereas CD4 regulatory T lymphocytes may play a central role in the control of neutrophil recruitment in indirect ALI.

The first signs and symptoms of ARDS are a feeling that one cannot get enough air into the lungs, rapid breathing, and low oxygen levels hi the blood. Other signs and symptoms of ARDS are clicking, bubbling, or rattling sounds in the lungs when breathing.

A variety of insults resulting in damage either to the vascular endothelium or to the alveolar epithelium could result in ARDS. ARDS may be caused by a viral infection (e.g., a coronavirus infection), sepsis, pneumonia, severe trauma and tissue injury, alcoholism, drug overdose, breathing in harmful fumes or smoke, and inhaling vomited stomach contents from the mouth. ARDS tends to develop within 48 hours of the event that caused it and it can worsen rapidly.

Treatment focuses on supporting the subject while the lungs heal. The goal of supportive care is to get enough oxygen into the blood and delivered to the body to prevent damage and to remove the injury that caused ARDS to develop.

Oxygen alone is usually not enough, and high levels of oxygen can also injure the lung. A ventilator is a machine used to open airspaces that have shut down and help with the work of breathing. The ventilator is connected to the patient through a mask on the face or a tube inserted into the windpipe.

A subject with ARDS is typically in bed on their back. When oxygen and ventilator therapies are at high levels and blood oxygen is still low, subject with ARDS is sometimes turned over on their stomach to get more oxygen into the blood.

Doctors may give a subject with ARDS a medication to relieve symptoms, treat the underlying cause, or prevent complications from being in a hospital. Such medications may include: acid-reducing medicines to prevent stress ulcers, which can cause bleeding in the intestines; antibiotics to treat or prevent infections; blood thinners, e.g., heparin, to stop blood clots from forming or growing larger; muscle relaxants to help prevent coughing or gagging while on a ventilator or to reduce the amount of oxygen the body needs; pain relievers; sedatives to help relieve anxiety, make it easier to breathe on a ventilator, or lower oxygen needs; and diuretics to increase urination to remove excess fluid from the body to help prevent fluid from building up in the lungs.

In some instances the subject with ARDS may be diagnosed as having a coronavirus infection. A coronavirus infection is caused by a coronavirus. Coronaviruses constitute the subfamily orthocoronavirinae in the family Coronaviridae. Coronaviruses often cause illness ranging from the common cold to more severe diseases, such as COVID-19 (a SARS-CoV2 infection), Middle East Respiratory Syndrome (MERS-CoV), Severe Acute Respiratory Syndrome (SARS-CoV), HCoV NL63, and HKU1. Coronaviruses are typically zoonotic. Common symptoms of a coronavirus infection include fever, sore throat, runny nose, sneezing, nasal congestion, snoring, coughing, dry cough, shortness of breath, difficulty breathing, persistent pain or pressure in the chest, dyspnea, pneumonia, acute respiratory syndrome, cyanosis, myalgia, headache, encephalopathy, myocardial injury, heart failure, arrhythmia, coagulation dysfunction, acute kidney injury, confusion or inability to arouse, fatigue, and gastrointestinal symptoms. In more severe cases, a coronavirus infection may cause pneumonia, severe acute respiratory syndrome, kidney failure, and even death. A subject may be predisposed to a severe case of a coronavirus infection (e.g., a SARS-CoV-2 infection). For example, a subject predisposed to a severe case of a coronavirus infection (e.g., a SARS-CoV-2 infection) may be 70 years or more of age, have diabetes mellitus, have a systolic blood pressure 150 mm Hg, have a known respiratory disease, have known heart failure, have known coronary disease, have had a fever of ≥38.4° C. within the last 48 hours, have dyspnea at the time of presentation, have bicytopenia, have pancytopenia, or have a combination of high neutrophil count and low lymphocyte count.

Advantageously, colchicine therapy described herein may reduce lethal outcomes in the treated subjects relative to the untreated subjects, the need for mechanical ventilation for the treated subjects relative to the untreated subjects, or, for a subject with a viral infection (e.g., a coronavirus infection) the viral load in the treated subjects relative to the untreated subjects.

Colchicine is preferably formulated into pharmaceutical compositions for administration to human subjects in a biologically compatible form suitable for administration in vivo. Pharmaceutical compositions described herein typically include colchicine and a pharmaceutically acceptable excipient.

Colchicine may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time. Preferably, colchicine is administered orally.

For human use, colchicine can be administered alone or in admixture with a pharmaceutical carrier selected with regard to the intended route of administration and standard pharmaceutical practice. Pharmaceutical compositions thus can be formulated in a conventional manner using one or more physiologically acceptable carriers comprising excipients and auxiliaries that facilitate processing of colchicine into preparations which can be used pharmaceutically.

This invention also includes pharmaceutical compositions which can contain colchicine and one or more pharmaceutically acceptable carriers. In making the pharmaceutical compositions of the invention, the active ingredient (colchicine) is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy*, 21$^{st}$ Ed., Gennaro, Ed., Lippencott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The dosage of colchicine used in the methods described herein can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. Colchicine may be administered initially in a suitable dosage that may be adjusted as required, depending on the clinical response. In general, a suitable daily dose of a compound of the invention may be that amount of the compound that is the lowest dose effective to produce a therapeutic effect. Such an effective dose may depend upon the factors described above.

Colchicine may be administered to the patient in a single dose or in multiple doses. When multiple doses are administered, the doses may be separated from one another by, for example, multiple hours. The compound may be administered according to a schedule or the compound may be administered without a predetermined schedule. Colchicine may be administered, for example, 1, 2, or 3 times per day. It is to be understood that, for any particular subject, specific dosage regimes should be adjusted over time according to the individual need and the professional judgment of the person administering or supervising the administration of the compositions. Preferably, colchicine is administered daily (e.g., once or twice daily). For example, colchicine may be administered twice daily for 3 days followed by once daily (e.g., for 27 days).

While the attending physician ultimately decide the appropriate amount and dosage regimen, an effective amount of colchicine may be, for example, a total daily dosage of, e.g., between 0.3 mg and 2.4 mg of colchicine. Preferably the daily dosage is 1.0 mg for the first three days of treatment, followed by a daily dose of 0.5 mg for the remainder of the treatment (e.g., 27 days). An effective daily dosage for subjects between 4 and 6 years old may be, for example, between 0.3 and 1.8 mg of colchicine. An effective daily dosage of subjects between 6 and 12 years old may be, for example, between 0.9 and 1.8 mg of colchicine. An effective daily dosage for subjects older than 12 years may be, for example, between 1.2 and 2.4 mg of colchicine.

Colchicine may be administered to subjects with a pharmaceutically acceptable excipient in a unit dosage form. The chemical compounds for use in such therapies may be produced and isolated by any standard technique known to those in the field of medicinal chemistry. Conventional pharmaceutical practice may be employed to provide suitable formulations or compositions to administer colchicine to subjects. Administration may begin before the patient is symptomatic.

Exemplary routes of administration of colchicine include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. Colchicine is desirably administered with a pharmaceutically acceptable excipient. Pharmaceutical formulations of colchicine formulated for treatment of the disorders described herein are also part of the present invention. Preferably, the route of administration is oral administration.

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution- or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Dosages for buccal or sublingual administration may be determined as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices typically include a compound of the invention with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of compounds of the invention. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., Biesalski, U.S. Pat. No. 5,112,598 and Biesalski, U.S. Pat. No. 5,556,611, each of which is herein incorporated by reference).

In some embodiments, colchicine is administered in combination with a second therapeutic. Non-limiting examples of second therapeutics are an antiviral drug (e.g., remdesivir), an antimalarial drug, an anti-inflammatory drug (e.g., a steroid such as dexamethasone, parenteral immunoglobulin, or aspirin), an antibiotic, an acid-reducing medicine, a blood thinner, a muscle relaxant, a pain reliever, a sedative, or a diuretic. In other embodiments, the second therapeutic is convalescent plasma from a subject who has recovered from a coronavirus infection.

The following examples are meant to illustrate the invention. They are not meant to limit the invention in any way.

EXAMPLES

Example 1: Materials and Methods

The study protocol was approved by the animal research and ethics committees of the Montreal Heart
Institute and all experiments conducted in accordance with the Canadian guidelines for the care of laboratory animals.

Animal model and colchicine administration. Male Wistar rats weighing 250-300 g were purchased from Charles River, St. Constant, Québec. They were divided in three groups: Sham+placebo (n=8), oleic acid+placebo (n=8) and oleic acid+colchicine (n=8). Oleic acid (150 mg/kg in 0.3 cc) was prepared daily as a mixture with 0.1% bovine serum albumin (BSA) dissolved in distilled water, stored and protected from light at room temperature. Colchicine (1 mg/kg) or distilled water (placebo) was administered by daily gavage (in a volume up to 2 ml/kg) for three days before the induction of the ALI model. On the beginning of the fourth day a last forth dose of colchicine or placebo was administered and rats immediately injected via a jugular vein cannula with oleic acid or with 0.1% BSA. There was no death in the sham group. There was one death in the oleic acid+placebo group 3 hours after injection of oleic acid and prior to any measurement.

There was one surgical death in oleic acid+colchicine treatment by laceration of the jugular vein, prior to injection of oleic acid. Oleic acid was administered under ketamine/xylazine anesthesia by slow bolus injection over 30 seconds and the catheter was flushed with 0.3 ml of 0.1% BSA before and after injection. Four hours later, the animals were studied. Conscious unrestrained respiratory parameters were obtained by whole body plethysmography (Emka technologies). Rats were then anesthetized with 2.5% isoflurance and 100% oxygen (1 L/min) administered with a nose cone/face mask for a duration of 5 minutes before terminal exsanguination. 2 ml of arterial blood was collected through the thoracic aorta into a syringe containing lyophilized heparin for arterial blood gas assessment. The remaining blood was collected into EDTA Lavendar tubes for complete blood count and flow cytometry. Cytokines measurements were assessed with serum isolated with serum clot activator tubes.

The lungs were excised for analysis: the left lung was cannulated and perfusion-fixed with 10% buffered formalin for histology and immunohistochemistry. The right superior and middle lobes were used to measure the lung weight and edema. The inferior lobes of the right lung were snap-frozen and stored at −80° C. for gene expression analysis. Pulmonary edema was measured from the ratio of total divided by dry weight of the right lung. Total weight, including water, was measured and lung tissue was dried in an oven at 60° C. for 5 days and reweighed as dry weight.

Lung histology and immunohistology. All histological and immunohistological procedures were performed by the same person blinded to treatment assignment. The left lung was cannulated and perfused with 10% formalin PBS-buffered solution and fixed for 5 days. Tissues were dehydrated by incubating in a series of solutions with an increased ethanol content (70, 95, and 100%), followed by xylene, and embedded in paraffin. The specimens were cut into 6-μm sections, mounted on charged slides and processed with hematoxylin phloxine saffron (HPS) staining.

Immunohistological procedures were initiated by incubating the slides in citrate antigen retrieval (pH 6.0) and endogenous peroxidase blocking (3% hydrogen peroxide). Sections were then blocked by incubating in PBS containing 10% normal goat serum (same species as secondary antibody) for 60 minutes. Slides were incubated with a rabbit polyclonal anti-myeloperoxidase (MPO, Pa5-16672; ThermoFisher, MA USA) for neutrophil detection, with a rabbit polyclonal anti-histone H3 citrulline R2+R8+R17, (Cit-H3, ab5103; ABCAM, Cambridge, United Kingdom) for NETosis and primary antibodies were omitted for negative controls. After washing, sections were incubated with a biotinylated secondary antibody (Vector Laboratories, Burlingame, Calif.) for 30 minutes, washed, then incubated with avidin-biotin complex (ABC kit) and visualized using diaminobenzidine substrate (Vector Laboratories) (27-29).

The HPS slides were scanned to get a picture of the whole left lung (Super coolscan 5000; Nikon, Tokyo Japan). Using a brightfield microscope (BX45, Olympus, Richmond Hill, ON, Canada), images were acquired under 200× magnification on the most damaged/altered regions, acquiring 5 fields per slide for the HPS staining and 10 fields per slide for IHC (MPO and Cit-H3) staining. For the HPS staining, the following analyses were performed: 1) thickness of alveolar membranes, 2) percentage (%) of altered lung tissue, and 3) injury score of the lungs.

To assess the thickness of alveolar membranes, 20 measurements per field were performed (corresponding to 100 measurements per slide) and were expressed as the mean thickness (μm) of the alveolar membranes. A morphometric analysis has been performed to assess the percentage of altered lung tissue over total lung area (excluding trachea, major bronchi, and blood vessels >700 μm diameter). To evaluate lung injury, we used an adapted version of the standardized histology score from the American Thoracic Society Documents (30). The histology scores (0, 1 or 2), were given for: 1) neutrophils in the alveolar space, 2) neutrophils in the interstitial space, 3) proteinaceous debris, 4) alveolar septal thickening, 5) alveolar hemorrhage, 6) interstitial space/membrane hemorrhage, and 7) alveolar necrosis. For each slide the maximal injury score, corresponding to the sum of the score (score 0 to 2) of the 7 parameters×5 fields per slide, is 70 points (2×7×5).

Neutrophil immunoreactivity in the lungs was performed to assess the presence of neutrophils (MPO immunostaining) and neutrophils undergoing NETosis (Cit-H3). The percent area (%) occupied by neutrophils in the lungs was quantified by color segmentation and represented as the MPO area over total lung tissue area. To assess neutrophils undergoing NETosis, we quantified the intensity of Cit-H3 staining (lumen).

All analyses were performed using Image Pro Premier version 3.0 software (Media Cybernetics, Rockville, Md., USA).

Serum cytokine quantification. Quantitative determination of serum IFN-γ, IL-1β, IL-4, IL-5, IL-6, KC/GRO, IL-10, IL-13, and TNF-α was done using the electrochemiluminescence-based Meso Scale Discovery (MSD) platform (Rockville, Md., USA). Proteins levels were measured in a multiplex assay using the V-PLEX Proinflammatory Panel 2 Rat kit (MSD). Samples were diluted 1:5 in proprietary buffer (MSD) and measured. Data were acquired using a MESO QuickPlex SQ 120 plate reader (MSD) and protein concentrations were determined using the MSD Discovery Workbench 4.0 analysis software. All values reported are between the lower and the upper limits of quantification of the kit. Quantitative determination of serum Cit-H3 was measured by a commercially available ELISA kit (Cayman Chemical, 501620, Ann Arbor, Mich., USA).

Flow Cytometry

In vitro LPS challenge of blood leukocytes. Whole blood samples collected on EDTA-coated tubes were incubated, or not, with LPS (500 ng/mL) for 30 minutes at 37° C. The samples were then stained using mouse anti-rat CD45 Alexa Fluor 700 (clone OX-1, conjugated to Alexa Fluor 700, Biolegend), mouse anti-rat CD11 b antibody (clone WT.5, conjugated to V450, BD Horizon), and 7AAD (Biolegend) for 30 minutes at 4° C. FACS lysing solution (BD Pharm Lyse, BD Biosciences) was added for 15 minutes at room temperature and samples were stored at 4° C. until analysis by flow cytometry (LSRII, BD Biosciences). Data were analyzed on Diva software version 8.0.1 (BD Biosciences).

Leukocyte immunophenotyping. Using reverse pipetting, 100 μl of whole blood collected on EDTA-coated tubes were incubated with anti-CD32 to prevent FC-mediated non-specific binding according to the manufacturer's instructions. The panel of antibodies as well as the gating strategy were inspired by Barnett-Vanes and al., PLoS One 2016; 11:e0142520.

Briefly, a panel of 11 antibodies (Table 1) was used to identify the neutrophils (CD45$^+$/SSChi/His48$^+$), the monocytes (CD45$^+$/SSC$^{lo}$/His48$^{hi\ or\ lo}$/CD43$^{hi\ or\ lo}$), the B lymphocytes (CD45$^+$/SSC$^{lo}$/CD45R$^-$B220$^+$), the T lymphocytes (CD45$^+$/SSC$^{lo}$/CD3$^+$/CD4$^+$ or CD8$^+$), and the natural killer cells (CD45$^+$/SSC$^{lo}$/CD161a$^+$). The whole blood samples were incubated with the antibodies for 20 minutes at room temperature and the BD Pharm Lyse solution was then added for 10 minutes to lyse the erythrocytes. Samples were stored at 4° C. until analysis by flow cytometry (LSRII BD Biosciences). Accucount (Spherotech) was added to establish a cell count per μl of blood. Data were analyzed on Diva software version 8.0.1 (BD Biosciences). The antibodies are listed in Table 1, below.

TABLE 1

Monoclonal antibodies used for the identification of leukocyte subpopulations

| Antibody | Fluorochrome | Clone | Supplier | Dilution |
| --- | --- | --- | --- | --- |
| Live-Dead | 7AAD | | Biolegend | 1/20 |
| CD32 | N/A | | BD | 1/100 |
| CD45 | Alexa Fluor 700 | OX-1 | Biolegend | 1/100 |
| Granulocytes | FITC | HIS48 | BD Pharmingen | 1/200 |
| CD11b | V450 | WT.5 | BD Horizon | 1/100 |
| CD43 | PE | W3/13 | Biolegend | 1/200 |
| CD45R (B220) | BV711 | HIS24 | BD Horizon | 1/50 |
| CD3 | BV605 | 1F4 | BD Horizon | 1/50 |
| CD4 | APC-Cy7 | OX-35 | BD Pharmingen | 1/50 |
| CD8a | BV786 | OX-8 | BD Horizon | 1/50 |
| CD161 | Alexa Fluor 647 | 10/78 | BD Pharmingen | 1/400 |

RNA Extraction and Quantification of mRNA Expression by RT-QPCRANALYSIS

Tissue homogenization, RNA extraction, RT-PCR, and real-time PCR. About 30mg of rat lung samples were homogenized in a TissueLyser II (Qiagen, Germany) in 700 μL of RLT buffer from the RNeasy Mini RNA extraction kit (Qiagen, Germany) supplemented with the anti-foam DX Reagent. Total RNA was extracted according to the kit's instructions. RNA integrity and quantity were assessed using a 2100 Bioanalyzer Instrument (Agilent, Santa Clara, Calif.). 500 ng of RNA were used for cDNA synthesis using the High-Capacity cDNA Reverse Transcription Kit (Applied Biosystems, Foster City, Calif.). For RT-qPCR, reactions were performed in duplicates using the SsoAdvanced Universal SYBR Green Supermix (Bio-Rad, Hercules, Calif.), 2.5 ng of cDNA and a final concentration of 100 nM of each primer. The cycling protocol started with a denaturation step at 95° C. for 5 min, followed by 40 cycles of denaturation at 95° C. for 15 seconds and primer annealing and extension at 57° C. for 30 seconds. Upon completion of the cycling steps, a melting curve protocol was performed from 60° C. to 95° C. and the reaction was stored at 4° C. Real-time PCR was carried out using a CFX384 Touch Real-Time PCR Detection System (Bio-Rad, Hercules, Calif.). The geometric mean of housekeeping genes ACTB, GAPDH, and XBP1 was used as an internal control to normalize the variability in expression levels which were analyzed using the $2^{-\Delta\Delta CT}$ method. Heat maps of normalized expression values for gene expression was generated using Morpheus from Broad Institute available online from broadinstitute.org. To normalize the data, the $\log_2$ of normalized expression values for IL-2, IL-13, CXCR2, E-sel, Arg1, CXCL1, CalCRL, Ramp2, and ATP1B1 were used. The primer sequences are provided in Table 2, below.

TABLE 2

Primer sequences used for quantitative real-time PCR of rat target genes.

| Gene | Forward primer (5'-3') | Reverse primer (5'-3') |
|---|---|---|
| ACTB | CCCTAAGGCCAACCGTGAA (SEQ ID NO:1) | GAGGCATACAGGGACAACACAG (SEQ ID NO:2) |
| Arg1 | GCAGAGACCCAGAAGAATG (SEQ ID NO:3) | GCCAGAGATGCTTCCAAT (SEQ ID NO:4) |
| ATP1A1 | TGCTCTCTCCTCTTTCTA (SEQ ID NO:5) | CTTCTTGCTCTTCTTGTC (SEQ ID NO:6) |
| ATP1B1 | GCTAAACATCATCAGGTTCCT (SEQ ID NO:7) | TTGGGTTCACTGGGCATA (SEQ ID NO:8) |
| Calcrl | GTTCAGACATCCAGATAGTAA (SEQ ID NO:9) | GAGAGGCAATAGATAATCCAT (SEQ ID NO:10) |
| Casp1 | CGAGACCTGTGCGATCAT (SEQ ID NO:11) | GCTGATGGACCTGACTGAA (SEQ ID NO:12) |
| CD31 | TCATTGGAGTGGTCATTG (SEQ ID NO:13) | TGTTGGAGTTCAGAAGTG (SEQ ID NO:14) |
| CD68 | AAGCAGCACAGTGGACAT (SEQ ID NO:15) | TTGTATTTCCGCAACAGAAGC (SEQ ID NO:16) |
| CXCL1 | TCATAGCCACACTCAAGAA (SEQ ID NO: 17) | GGACACCCTTTAGCATCT (SEQ ID NO:18) |
| CXCR2 | AAGCCTTGAGTCACAGAG (SEQ ID NO:19) | AATATCTCCACTGAAGAAGTCT (SEQ ID NO:20) |
| E-sel | GTCCAGTTGTAAGTTCTC (SEQ ID NO:21) | ACTCATGTTCATCTTTCC (SEQ ID NO:22) |
| GAPDH | GGCTGGCATTGCTCTCA (SEQ ID NO:23) | GTCCACCACCCTGTTGCTGTA (SEQ ID NO:24) |
| GPR84 | TCAGGTGAGTCTCCATCAT (SEQ ID NO:25) | AACAGGGTGAGCACATTG (SEQ ID NO:26) |
| ICAM-1 | TTGGAGACTAACTGGATGA (SEQ ID NO:27) | CTCTGGGAACGAATACAC (SEQ ID NO:28) |
| IL-1b | GACAGAACATAAGCCAACA (SEQ ID NO:29) | ACACAGGACAGGTATAGATT (SEQ ID NO:30) |
| IL-6 | TGAAGAACAACTTACAAGATAAC (SEQ ID NO:31) | CATTAGGAGAGCATTGGAA (SEQ ID NO:32) |
| IL10 | AGCAGGTGAAGAATGATT (SEQ ID NO:33) | GCAGTTGATGAAGATGTC (SEQ ID NO:34) |
| IL13 | CACAAGACCAGAAGACTT (SEQ ID NO:35) | GCCATTCAATATCCTCTG (SEQ ID NO:36) |
| IL33 | CACACTGAGTATCCAAGG (SEQ ID NO:37) | CGTAACATCCATTCTCCAA (SEQ ID NO:38) |
| MCP-1 | TCACCAGCAGCAGGTGTCC (SEQ ID NO:39) | CACAGATCTCTCTCTTGAGCTTGG (SEQ ID NO:40) |
| MMP2 | CACAACCAACTACGATGATGA (SEQ ID NO:41) | GCTGCCACAAGGAATAGG (SEQ ID NO:42) |
| MMP9 | CCGACTTATGTGGTCTTCC (SEQ ID NO:43) | CAGGTAATCCTCTGCCAG (SEQ ID NO:44) |
| NLRP3 | TAAGAAGGACCAGCCAGAG (SEQ ID NO:45) | CGAGATGCGGGAGAGATA (SEQ ID NO:46) |
| PAI-1 | GATGCTATGGGATTCAAT (SEQ ID NO:47) | GTACTGATCTCATTCTTGT (SEQ ID NO:48) |
| Ramp1 | TGTCAAAAGGGAAGATGGA (SEQ ID NO:49) | GTTGCTGTAATACCTGCTAAT (SEQ ID NO:50) |
| SCNN1A | ATCAACCTCAATTCAGACAAG (SEQ ID NO:51) | GCGAGTGTAGGAAGAGTT (SEQ ID NO:52) |
| SCNN1G | CTGTGATGCCAGGAACTTC (SEQ ID NO:53) | ATGGAGGTGCTGAGGATG (SEQ ID NO:54) |
| TIMP-1 | ACACGCTAGAGCAGATAC (SEQ ID NO:55) | GCTGGTATAAGGTGGTCTC (SEQ ID NO:56) |
| TNFa | GTGATCGGTCCCAACAAGGA (SEQ ID NO:57) | GATGAGAGGGAGCCCATTTG (SEQ ID NO:58) |
| VCAM-1 | GCCTCGCTAAGTTACACAG (SEQ ID NO:59) | AGCAGGTCAGGTTCACAG (SEQ ID NO:60) |
| XBP1 | AAGTGGTGGATTTGGAAGAAG (SEQ ID NO:61) | CCTTGGACTCTGCCTCTG (SEQ ID NO:62) |

Statistical analysis. Comparisons between groups were performed by one-way ANOVA followed by Tukey's post-hoc comparisons. Significant differences were considered if $p<0.05$. All values are presented as mean±SEM.

Effects of colchicine on lung edema and gas exchanges. Oleic acid induced severe ALI with almost tripling of lung weight and severe edema evidenced by increased wet/dry lung weight ratio. Macroscopically, the lungs were larger and hemorrhagic. There was severe respiratory failure with markedly reduced blood oxygenation. The animals were administered 100% $FiO_2$ before arterial blood gas sampling so that the measured $PaO_2$ is equivalent to the $PaO_2/FiO_2$, a recognized parameter indicative of ARDS severity. Clinical ARDS is recognized when the $PaO_2/FiO_2$ is less than 300. Oleic acid caused severe respiratory failure as the $PaO_2$ decreased from 380±18 mmHg to 66±13 mmHg (mean±SEM) with $CO_2$ retention causing respiratory acidosis. Colchicine therapy reduced pulmonary edema, markedly improved blood oxygenation with a $PaO_2$ of 246±45 mmHg, and reduced respiratory acidosis. These results are summarized in FIG. 1.

Effects of colchicine on respiratory parameters, blood cell counts, and biochemistry. Animals with oleic acid injury had increased respiratory rate with lowertidal volume. Both were improved although non-significantly with colchicine therapy. Oleic acid injection caused an increase in blood hemoglobin and hematocrit, the latter being statistically significant. Colchicine therapy normalized both hemoglobin and hematocrit, the latter being no longer significantly different from those of the sham animals. Oleic acid increased leukocyte count, the increase being statistically significant in the colchicine treated animals compared to the sham group. This increase was mostly caused by an elevation in neutrophils, also significant in the colchicine treated animals only. The data are summarized in Table 3, below.

reduced by oleic acid and improved by colchicine. There was no difference on corrected calcium, lactates, and bicarbonates between groups.

Figure 2:
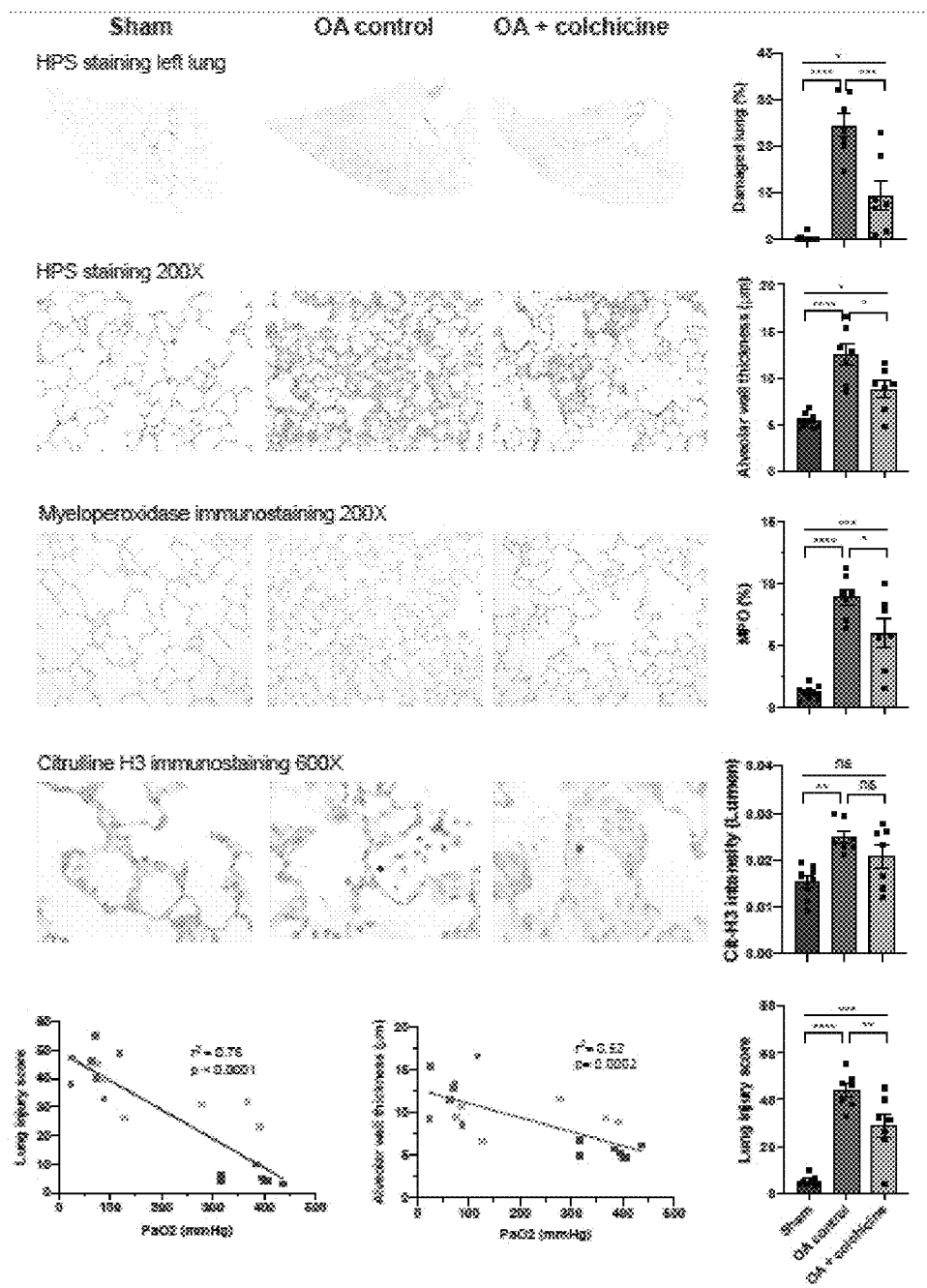
FIG. 2 is a series of images and graphs showing the effects of colchicine therapy on lung injury, neutrophils recruitment, and NETosis after oleic acid-induced ALI. Shown are, left to right in the bar graphs, the control (Sham), oleic acid-induced ALI (OA control), and oleic acid induced ALI with colchicine (OA+colchicine). Values are mean±SEM. **$p<0.0001$;*$p<0.001$, **$p<0.01$; * $p<0.05$.

Effects of colchicine on lung injury, neutrophil recruitment, and NETs formation. All samples were analyzed by a technician blinded to treatment assignment. Oleic acid caused important histological lung injury. Representative examples of the appearance of the complete left lung at low magnification demonstrates evident zones of severe damage, which are markedly reduced in colchicine-treated animals. The proportion of injured area in the oleic acid ALI group was 24.6±2.4% with a 61% relative reduction down to 9.6±3.1% after colchicine treatment. The lung injury score (maximum score of 70) was markedly elevated after oleic acid from 5.1±0.8 in sham to 44±2.8, and markedly reduced by colchicine to 28.7±5.0. Mean alveolar wall thickness more than doubled after oleic acid from 4.6±0.3 pm to 10.9±1.1 μm and this was also significantly reduced by colchicine to 7.8±1.1 μm. Both the lung injury score and alveolar wall thickness were inversely correlated with the severity of ARDS measured from the PaO2. Lung neutrophil recruitment, as assessed by MPO immunostaining, was greatly increased after ALI from 1.16±0.19% to 8.86±0.66% and significantly reduced by colchicine therapy to 5.95±1.13%. Lung neutrophils undergoing NETosis were assessed by measuring citrullinated histone H3 (Cit-H3) immunostaining intensity. These results are summarized in FIG. 2.

Figure 5:
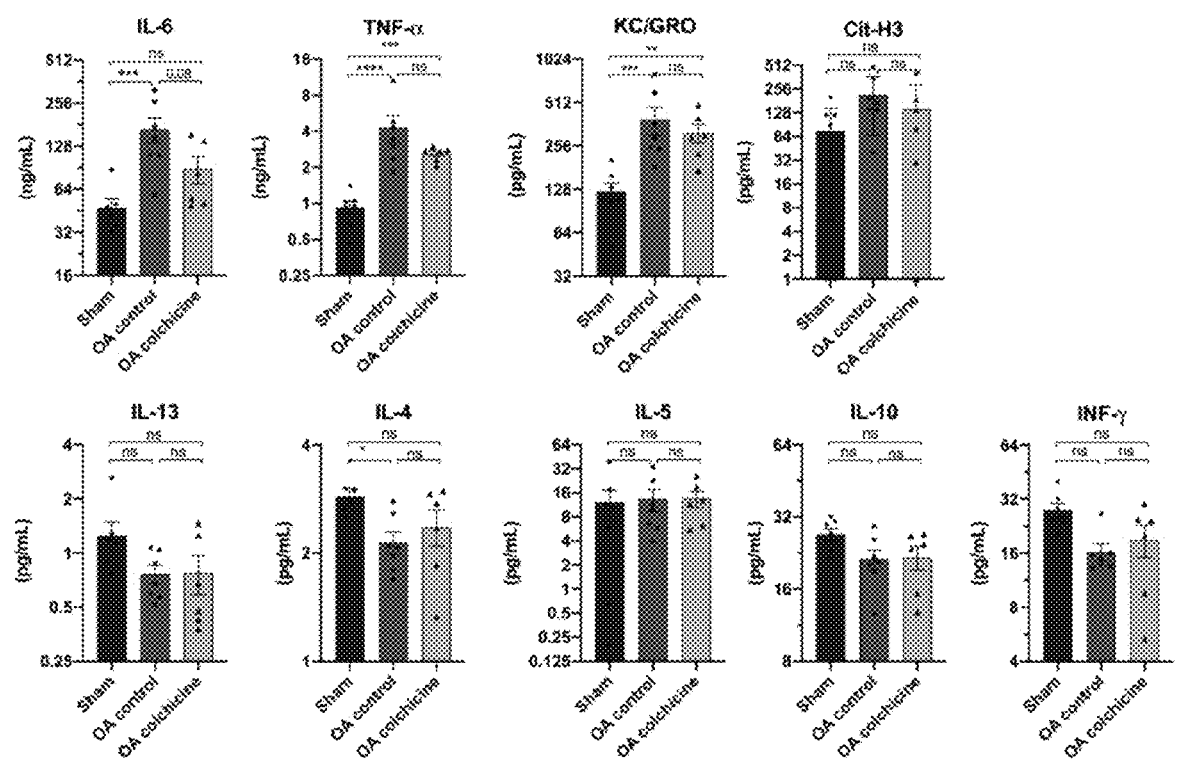
FIG. 5 is a series of graphs showing the effects of colchicine therapy on plasma cytokines and NETs 4 hours after oleic acid ALI. Shown are, left to right in the bar graphs, the control (Sham), oleic acid-induced ALI (OA control), and oleic acid induced ALI with colchicine (OA+colchicine). Values are mean±SEM. **$p<0.0001$; *$p<0.001$, **$p<0.01$; *$p<0.05$.

Treatment with oleic acid increased basal NETosis by 63%, whereas colchicine therapy nearly halved the induction of NETosis, bringing it back to a 35% increase over basal level, a value no longer statistically different from the control group. As shown in FIG. 5, oleic acid-induced ALI was associated with an increase in mean serum IL-6, TNF-α, and KC/GRO.

TABLE 3

Effect of colchicine on respiratory parameters, blood cell counts, and biochemistry

| | Sham | OA control | OA + colchicine |
|---|---|---|---|
| Breathing rate (bpm) | 102 ± 6 | 181 ± 10*** | 166 ± 20** |
| Tidal volume (ml) | 2.67 ± 0.15 | 1.19 ± 0.05*** | 1.81 ± 0.35* |
| Peek inspiratory flow (ml/s) | 16.01 ± 1.23 | 16.43 ± 0.80 | 17.75 ± 2.72 |
| Peek expiratory flow | 15.48 ± 1.16 | 11.83 ± 0.68 | 13.19 ± 1.41 |
| Hemoglobin (g/L) | 150 ± 2 | 158 ± 3 | 153 ± 2 |
| Hematocrit (%) | 45.0 ± 0.6 | 48.7 ± 0.8** | 46.6 ± 0.5 |
| Leukocytes ($10^9$/L) | 2.32 ± 0.29 | 3.75 ± 0.49 | 4.90 ± 0.68** |
| Platelets ($10^9$/L) | 1029 ± 15 | 844 ± 57* | 986 ± 56 |
| Neutrophils ($10^9$/L) | 1.14 ± 0.17 | 2.00 ± 0.35 | 2.71 ± 0.36** |
| Lymphocytes ($10^9$/L) | 1.31 ± 0.15 | 1.77 ± 0.18 | 2.19 ± 0.33 |
| Glucose (mmol/L) | 16.8 ± 1.3 | 27.0 ± 0.6**** | 21.7 ± 1.6*, †† |
| Sodium (mmol/L) | 143.7 ± 0.7 | 138.3 ± 0.9*** | 141.4 ± 0.9† |
| Calcium (mmol/L)[1] | 1.38 ± 0.01 | 1.42 ± 0.01 | 1.40 ± 0.01 |
| Lactate (mmol/L) | 2.31 ± 0.26 | 1.90 ± 0.37 | 2.4 ± 0.53 |
| Bicarbonate (mmol/L) | 26.0 ± 0.7 | 28.1 ± 1.1 | 27.6 ± 0.8 |

*, , *, **** is for $p < 0.05, 0.01, 0.001, 0.0001$ versus Sham, respectively.
†, †† is for $p < 0.05, 0.01$ versus OA + Placebo, respectively.
All values are mean ± SEM.
[1] Calcium corrected for pH.

There was a mild non-significant increase in lymphocytes after oleic acid, with no effect of colchicine therapy. Platelet count was significantly reduced by oleic acid injury, and partly normalized after colchicine therapy, being no-longer different from the sham group. Oleic acid caused a marked elevation of plasma glucose that was significantly reduced by colchicine therapy. Inversely, plasma natremia was There was a trend towards reduced IL-6 level with colchicine, and TNF-α and KC/GRO were also non-significantly reduced by therapy. There was no change in any of the other cytokines measured: Cit-H3, INF-γ, IL-10, IL-13, IL-4 and IL-5. IL-1 13 level was too low to be quantified in 14 of the 20 rats.

Figure 3:
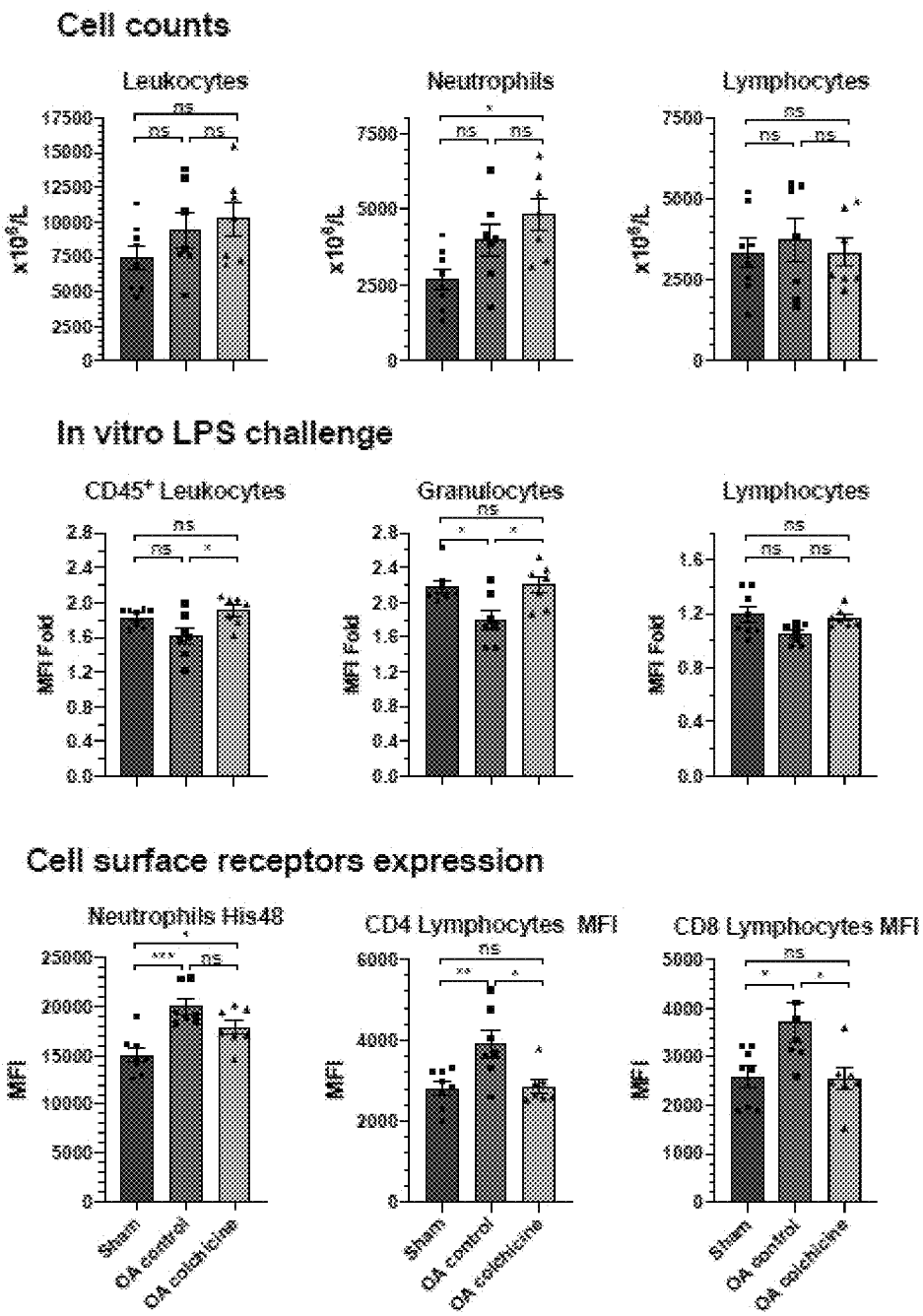
FIG. 3. is a series of graphs showing the results of whole blood flow cytometry analysis of leukocytes after oleic acid-induced ALI and effects of colchicine therapy. MFI=mean fluorescence intensity. Shown are, left to right in the bar graphs, the control (Sham), oleic acid-induced ALI (OA control), and oleic acid induced ALI with colchicine (OA+colchicine). Values are mean±SEM.*$p<0.001$, $p<0.01$; * $p<0.05$.

Effects of colchicine on blood leukocyte activation evaluated by flow cytometry. Leukocyte count on flow cytometry demonstrated an increase in neutrophils that was significant in colchicine treated animals, but no change in lymphocytes counts. A leukocyte activation assay was performed on rat blood samples obtained at the time of sacrifice by in vitro LPS stimulation (500 ng/mL) and analysis of the surface expression of CD11b, a member of the β2 integrin family. In sham-treated rats, LPS stimulation resulted in approximately a 2-fold increase of cell surface CD11b mean fluorescence intensity (MFI). Oleic acid exposure tended to decrease the response to LPS in leukocytes and significantly reduced the response in granulocytes, whereas colchicine restored the normal response to LPS stimulation. In unstimulated blood from oleic acid treated animals, we observed an increase in His48 fluorescence of neutrophils that was normalized by colchicine treatment. Additionally, cell surface CD4 and CD8 on respective lymphocyte sub-populations were increased after oleic acid stimulation, and also normalized by colchicine therapy. These results are summarized in FIG. 3.

Figure 4:
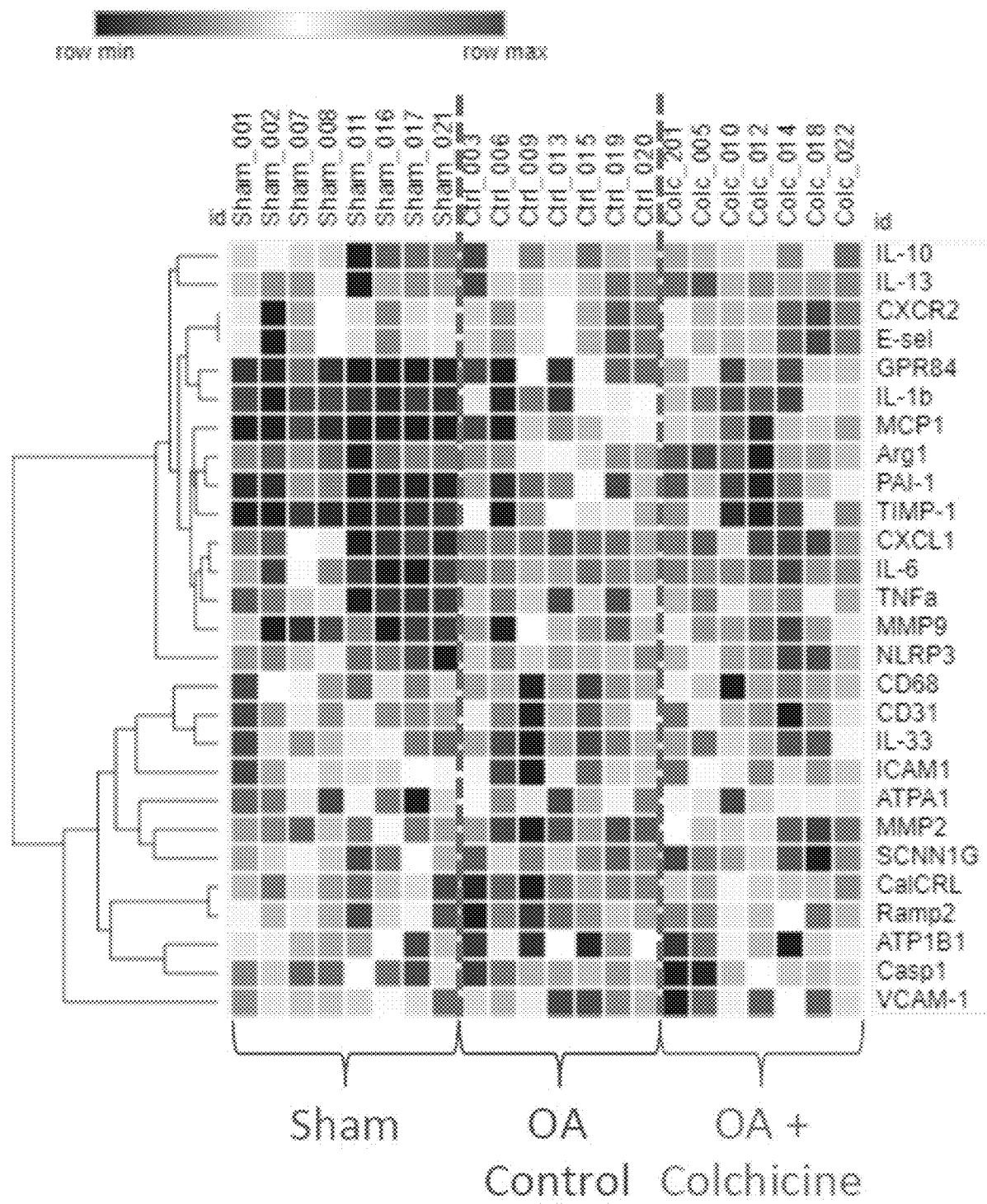
FIG. 4 is a clustered heatmap representation of unsupervised clustering of lung tissue mRNA expression of 27 selected markers of inflammation and injury. Shown are the control (Sham), oleic acid-induced ALI (OA control), and oleic acid induced ALI with colchicine (OA+colchicine).

Effects of colchicine on markers of inflammation and injury in lung tissue was determined for the control, oleic acid induced ALI, and oleic acid induced ALI with the administration of colchicine (FIG. 4). The mRNA expression of 27 genes involved in inflammatory responses and injury was measured in lung tissue. The results, summarized in a clustered heatmap, clearly demonstrate lung tissue transcriptional regulation of these genes in oleic acid-exposed rats. There was, however, no individual statistically significant effect of colchicine therapy.

REFERENCES

1. Bellani G et al., JAMA 2016; 315:788-800.
2. Thompson et al., N Engl J Med 2017; 377:1904-1905.
3. Fan et al., JAMA 2018; 319:698-710.
4. Sweeney et al., Lancet 2016; 388:2416-2430.
5. Wong et al., Ann Transl Med 2019; 7:504.
6. Prame et al., Cell Tissue Res 2018; 371:551-565.
7. Potey et al., J Pathol 2019; 247:672-685.
8. Herold et al., Front Immunol 2011; 2:65.
9. Venet et al., J Immunol 2009; 183:3472-80.
10. Tardif et al., N Engl J Med 2019; 381:2497-2505.
11. Safi et al., J Dermatol Sci 2018; 92:143-150.
12. Vaidya et al., medRxiv 2020:2020.04.20.20034025.
13. Otani et al., Sci Rep 2016; 6:32587.
14. Martinez et al., Atherosclerosis 2018; 269:262-271.
15. Martinez et al., J Am Heart Assoc 2015; 4:e002128.
16. Bursten et al., Crit Care Med 1996; 24:1129-36.
17. Goncalves-de-Albuquerque et al., Mediators Inflamm 2015; 2015:260465.
18. Beilman et al., Lipids 1995; 30:817-23.
19. Channappanavar et al., Semin Immunopathol 2017; 39:529-539.
20. Chen et al., Drug Des Devel Ther 2019; 13:1545-1554.
21. Chen et al., Front Microbiol 2019; 10:50
22. Zhang et al., Infect Immun 2012; 80:3634-41.
23. Li et al., J Proteome Res 2007; 6:1364-70.
24. Verrecchia et al., Mediators Inflamm 2017; 2017:7461426.
25. Ghio et al., J Appl Physiol (1985) 1991; 71:657-65.
26. Ozdemir et al., Neonatology 2012; 102:265-9.
27. Perdomo et al., Nat Commun 2019; 10:1322.
28. Nawaito et al., Am J Physiol Heart Circ Physiol 2019; 316:H1281-H1296.
29. Sinnathamby et al., J Cell Biochem 2015; 116:45-57.
30. Matute-Bello et al., Am J Respir Cell Mol Biol 2011; 44:725-38.
31. Barnett-Vanes et al., PLoS One 2016; 11:e0142520.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

All publications, patents, and patent applications are herein incorporated by reference in their entirety to the same extent as if each individual publication, patent, or patent application was specifically and individually indicated to be incorporated by reference in its entirety.

Other embodiments are in the claims.

What is claimed is:

1. A method of treating acute respiratory distress syndrome (ARDS) in a subject, the method comprising administering colchicine to the subject.

2. The method of claim 1, wherein the subject has a coronavirus infection.

3. The method of claim 2, wherein the coronavirus infection is a severe acute respiratory syndrome coronavirus 2 (SARS-CoV-2) infection.

4. The method of claim 2, wherein the subject has been diagnosed with COVID-19.

5. The method of claim 1, wherein the subject has sepsis, pneumonia, severe trauma and tissue injury, inhaled harmful fumes or smoke, or inhaled vomited stomach contents from the mouth.

6. The method of claim 1, wherein the colchicine is administered daily, or wherein the colchicine is administered once, twice, or three times a day.

7. The method of claim 1, wherein the colchicine is administered twice daily for 3 days.

8. The method of claim 7, wherein the colchicine is administered twice daily for 3 days followed by once daily.

9. The method of claim 8, wherein the once daily administration is for 27 days.

10. The method of claim 1, wherein 0.3 to 2.4 mg of colchicine is administered daily, wherein 0.3 to 1.8 mg of colchicine is administered daily, wherein 0.4 to 0.6 mg of colchicine is administered daily, or wherein 0.5 mg of colchicine is administered daily.

11. The method of claim 1, wherein the colchicine is in the form of a tablet.

12. The method of claim 1, wherein the administration is oral administration.

13. The method of claim 1, wherein the subject was diagnosed with ARDS within 24 hours prior to initiating the treatment.

14. The method of claim 1, wherein the administration of colchicine is initiated upon assessment in (a) an emergency department (ED), (b) a hospital, (c) a medical office setting, or (d) a coronavirus testing facility.

15. The method of claim 1, wherein treatment with colchicine reduces morbidity or mortality in the clinical course of ARDS, reduces symptoms caused by ARDS, or reduces the need for ventilator dependency.

16. The method of claim 1, wherein treatment with colchicine results in a decrease in one or more symptoms related to ARDS, wherein the one or more symptoms related to the ARDS is selected from the group consisting of a feeling that one cannot get enough aft into the lungs, rapid breathing, low oxygen levels in the blood, and clicking, bubbling, or rattling sounds in the lungs when breathing.

17. The method of claim 1, wherein the colchicine is administered in combination with a second therapeutic, wherein the second therapeutic is an antiviral drug, an antimalarial drug, an anti-inflammatory drug, an antibiotic, an acid-reducing medicine, a blood thinner, a muscle relaxant, a pain reliever, a sedative, or a diuretic, or wherein the second therapeutic is convalescent plasma from a subject who has recovered from a coronavirus infection.

18. The method of claim 1, wherein the subject is a human.

19. The method of claim 1, wherein the subject is 1 to 5 years old, wherein the subject is less than one year old, or wherein the subject is less than 21 years old.

20. The method of claim 1, wherein the subject is a pediatric or adolescent subject 0 to 19 years old.

* * * * *

UNITED STATES PATENT AND TRADEMARK OFFICE
CERTIFICATE OF CORRECTION

PATENT NO. : 11,844,771 B2
APPLICATION NO. : 17/714238
DATED : December 19, 2023
INVENTOR(S) : Jean-Claude Tardif et al.

It is certified that error appears in the above-identified patent and that said Letters Patent is hereby corrected as shown below:

In the Claims

Column 38, Claim 16, Line 28, replace "aft" with --air--.

Signed and Sealed this
Twenty-third Day of April, 2024

*Katherine Kelly Vidal*

Katherine Kelly Vidal
*Director of the United States Patent and Trademark Office*

SEQUENCE LISTING

```
<160> NUMBER OF SEQ ID NOS: 62

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
ccctaaggcc aaccgtgaa                                            19

<210> SEQ ID NO 2
<211> LENGTH: 22
<212> TYPE: DNA
<213> ORGANISM: Artificial Sequence
<220> FEATURE:
<223> OTHER INFORMATION: Synthetic Construct

<400> SEQUENCE: 2
```
gaggcataca gggacaacac ag                                              22

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
gcagagaccc agaagaatg                                                  19

<210> SEQ ID NO 4
<211> LENGTH: 18
<212> TYPE: DNA
<213> ORGANISM: Artificial Sequence
<220> FEATURE:
<223> OTHER INFORMATION: Synthetic Construct

<400> SEQUENCE: 4
gccagagatg cttccaat                                                   18

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5
tgctctctcc tctttcta                                                   18

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6
cttcttgctc ttcttgtc                                                   18

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
gctaaacatc atcaggttcc t                                               21

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct

<400> SEQUENCE: 8
ttgggttcac tgggcata                                                   18

<210> SEQ ID NO 9
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 9
gttcagacat ccagatagta a                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
gagaggcaat agataatcca t                                              21

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct

<400> SEQUENCE: 11
cgagacctgt gcgatcat                                                  18

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
gctgatggac ctgactgaa                                                 19

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
tcattggagt ggtcattg                                                  18

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
tgttggagtt cagaagtg                                                  18

<210> SEQ ID NO 15
<211> LENGTH: 18
<212> TYPE: DNA
<213> ORGANISM: Artificial Sequence
<220> FEATURE:
<223> OTHER INFORMATION: Synthetic Construct

<400> SEQUENCE: 15
aagcagcaca gtggacat                                                  18
```

```
<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
ttgtatttcc gcaacagaag c                                              21

<210> SEQ ID NO 17
<211> LENGTH: 19
<212> TYPE: DNA
<213> ORGANISM: Artificial Sequence
<220> FEATURE:
<223> OTHER INFORMATION: Synthetic Construct

<400> SEQUENCE: 17
tcatagccac actcaagaa                                                 19

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
ggacaccctt tagcatct                                                  18

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct

<400> SEQUENCE: 19
aagccttgag tcacagag                                                  18

<210> SEQ ID NO 20
<211> LENGTH: 22
<212> TYPE: DNA
<213> ORGANISM: Artificial Sequence
<220> FEATURE:
<223> OTHER INFORMATION: Synthetic Construct

<400> SEQUENCE: 20
aatatctcca ctgaagaagt ct                                             22

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct

<400> SEQUENCE: 21
gtccagttgt aagttctc                                                  18

<210> SEQ ID NO 22
<211> LENGTH: 18
<212> TYPE: DNA
<213> ORGANISM: Artificial Sequence
<220> FEATURE:
<223> OTHER INFORMATION: Synthetic Construct
```

```
<400> SEQUENCE: 22
actcatgttc atctttcc                                                       18

<210> SEQ ID NO 23
<211> LENGTH: 17
<212> TYPE: DNA
<213> ORGANISM: Artificial Sequence
<220> FEATURE:
<223> OTHER INFORMATION: Synthetic Construct

<400> SEQUENCE: 23
ggctggcatt gctctca                                                        17

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
gtccaccacc ctgttgctgt a                                                   21

<210> SEQ ID NO 25
<211> LENGTH: 19
<212> TYPE: DNA
<213> ORGANISM: Artificial Sequence
<220> FEATURE:
<223> OTHER INFORMATION: Synthetic Construct

<400> SEQUENCE: 25
tcaggtgagt ctccatcat                                                      19

<210> SEQ ID NO 26
<211> LENGTH: 18
<212> TYPE: DNA
<213> ORGANISM: Artificial Sequence
<220> FEATURE:
<223> OTHER INFORMATION: Synthetic Construct

<400> SEQUENCE: 26
aacagggtga gcacattg                                                       18

<210> SEQ ID NO 27
<211> LENGTH: 19
<212> TYPE: DNA
<213> ORGANISM: Artificial Sequence
<220> FEATURE:
<223> OTHER INFORMATION: Synthetic Construct

<400> SEQUENCE: 27
ttggagacta actggatga                                                      19

<210> SEQ ID NO 28
<211> LENGTH: 18
<212> TYPE: DNA
<213> ORGANISM: Artificial Sequence
<220> FEATURE:
<223> OTHER INFORMATION: Synthetic Construct

<400> SEQUENCE: 28
ctctgggaac gaatacac                                                       18

<210> SEQ ID NO 29
```

```
<211> LENGTH: 19
<212> TYPE: DNA
<213> ORGANISM: Artificial Sequence
<220> FEATURE:
<223> OTHER INFORMATION: Synthetic Construct

<400> SEQUENCE: 29
gacagaacat aagccaaca                                                      19

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
acacaggaca ggtatagatt                                                     20

<210> SEQ ID NO 31
<211> LENGTH: 23
<212> TYPE: DNA
<213> ORGANISM: Artificial Sequence
<220> FEATURE:
<223> OTHER INFORMATION: Synthetic Construct

<400> SEQUENCE: 31
tgaagaacaa cttacaagat aac                                                 23

<210> SEQ ID NO 32
<211> LENGTH: 19
<212> TYPE: DNA
<213> ORGANISM: Artificial Sequence
<220> FEATURE:
<223> OTHER INFORMATION: Synthetic Construct

<400> SEQUENCE: 32
cattaggaga gcattggaa                                                      19

<210> SEQ ID NO 33
<211> LENGTH: 18
<212> TYPE: DNA
<213> ORGANISM: Artificial Sequence
<220> FEATURE:
<223> OTHER INFORMATION: Synthetic Construct

<400> SEQUENCE: 33
agcaggtgaa gaatgatt                                                       18

<210> SEQ ID NO 34
<211> LENGTH: 18
<212> TYPE: DNA
<213> ORGANISM: Artificial Sequence
<220> FEATURE:
<223> OTHER INFORMATION: Synthetic Construct

<400> SEQUENCE: 34
gcagttgatg aagatgtc                                                       18

<210> SEQ ID NO 35
<211> LENGTH: 18
<212> TYPE: DNA
<213> ORGANISM: Artificial Sequence
<220> FEATURE:
<223> OTHER INFORMATION: Synthetic Construct

<400> SEQUENCE: 35
```

```
cacaagacca gaagactt                                                18

<210> SEQ ID NO 36
<211> LENGTH: 18
<212> TYPE: DNA
<213> ORGANISM: Artificial Sequence
<220> FEATURE:
<223> OTHER INFORMATION: Synthetic Construct

<400> SEQUENCE: 36
gccattcaat atcctctg                                                18

<210> SEQ ID NO 37
<211> LENGTH: 18
<212> TYPE: DNA
<213> ORGANISM: Artificial Sequence
<220> FEATURE:
<223> OTHER INFORMATION: Synthetic Construct

<400> SEQUENCE: 37
cacactgagt atccaagg                                                18

<210> SEQ ID NO 38
<211> LENGTH: 19
<212> TYPE: DNA
<213> ORGANISM: Artificial Sequence
<220> FEATURE:
<223> OTHER INFORMATION: Synthetic Construct

<400> SEQUENCE: 38
cgtaacatcc attctccaa                                               19

<210> SEQ ID NO 39
<211> LENGTH: 19
<212> TYPE: DNA
<213> ORGANISM: Artificial Sequence
<220> FEATURE:
<223> OTHER INFORMATION: Synthetic Construct

<400> SEQUENCE: 39
tcaccagcag caggtgtcc                                               19

<210> SEQ ID NO 40
<211> LENGTH: 24
<212> TYPE: DNA
<213> ORGANISM: Artificial Sequence
<220> FEATURE:
<223> OTHER INFORMATION: Synthetic Construct

<400> SEQUENCE: 40
cacagatctc tctcttgagc ttgg                                         24

<210> SEQ ID NO 41
<211> LENGTH: 21
<212> TYPE: DNA
<213> ORGANISM: Artificial Sequence
<220> FEATURE:
<223> OTHER INFORMATION: Synthetic Construct

<400> SEQUENCE: 41
cacaaccaac tacgatgatg a                                            21

<210> SEQ ID NO 42
<211> LENGTH: 18
<212> TYPE: DNA
```

<213> ORGANISM: Artificial Sequence
<220> FEATURE:
<223> OTHER INFORMATION: Synthetic Construct

<400> SEQUENCE: 42
gctgccacaa ggaatagg                                                 18

<210> SEQ ID NO 43
<211> LENGTH: 19
<212> TYPE: DNA
<213> ORGANISM: Artificial Sequence
<220> FEATURE:
<223> OTHER INFORMATION: Synthetic Construct

<400> SEQUENCE: 43
ccgacttatg tggtcttcc                                                19

<210> SEQ ID NO 44
<211> LENGTH: 18
<212> TYPE: DNA
<213> ORGANISM: Artificial Sequence
<220> FEATURE:
<223> OTHER INFORMATION: Synthetic Construct

<400> SEQUENCE: 44
caggtaatcc tctgccag                                                 18

<210> SEQ ID NO 45
<211> LENGTH: 19
<212> TYPE: DNA
<213> ORGANISM: Artificial Sequence
<220> FEATURE:
<223> OTHER INFORMATION: Synthetic Construct

<400> SEQUENCE: 45
taagaaggac cagccagag                                                19

<210> SEQ ID NO 46
<211> LENGTH: 18
<212> TYPE: DNA
<213> ORGANISM: Artificial Sequence
<220> FEATURE:
<223> OTHER INFORMATION: Synthetic Construct

<400> SEQUENCE: 46
cgagatgcgg gagagata                                                 18

<210> SEQ ID NO 47
<211> LENGTH: 18
<212> TYPE: DNA
<213> ORGANISM: Artificial Sequence
<220> FEATURE:
<223> OTHER INFORMATION: Synthetic Construct

<400> SEQUENCE: 47
gatgctatgg gattcaat                                                 18

<210> SEQ ID NO 48
<211> LENGTH: 19
<212> TYPE: DNA
<213> ORGANISM: Artificial Sequence
<220> FEATURE:
<223> OTHER INFORMATION: Synthetic Construct

<400> SEQUENCE: 48
gtactgatct cattcttgt                                                19

<210> SEQ ID NO 49
<211> LENGTH: 19
<212> TYPE: DNA
<213> ORGANISM: Artificial Sequence
<220> FEATURE:
<223> OTHER INFORMATION: Synthetic Construct

<400> SEQUENCE: 49
tgtcaaaagg gaagatgga                                                    19

<210> SEQ ID NO 50
<211> LENGTH: 21
<212> TYPE: DNA
<213> ORGANISM: Artificial Sequence
<220> FEATURE:
<223> OTHER INFORMATION: Synthetic Construct

<400> SEQUENCE: 50
gttgctgtaa tacctgctaa t                                                 21

<210> SEQ ID NO 51
<211> LENGTH: 21
<212> TYPE: DNA
<213> ORGANISM: Artificial Sequence
<220> FEATURE:
<223> OTHER INFORMATION: Synthetic Construct

<400> SEQUENCE: 51
atcaacctca attcagacaa g                                                 21

<210> SEQ ID NO 52
<211> LENGTH: 18
<212> TYPE: DNA
<213> ORGANISM: Artificial Sequence
<220> FEATURE:
<223> OTHER INFORMATION: Synthetic Construct

<400> SEQUENCE: 52
gcgagtgtag gaagagtt                                                     18

<210> SEQ ID NO 53
<211> LENGTH: 19
<212> TYPE: DNA
<213> ORGANISM: Artificial Sequence
<220> FEATURE:
<223> OTHER INFORMATION: Synthetic Construct

<400> SEQUENCE: 53
ctgtgatgcc aggaacttc                                                    19

<210> SEQ ID NO 54
<211> LENGTH: 18
<212> TYPE: DNA
<213> ORGANISM: Artificial Sequence
<220> FEATURE:
<223> OTHER INFORMATION: Synthetic Construct

<400> SEQUENCE: 54
atggaggtgc tgaggatg                                                     18

<210> SEQ ID NO 55
<211> LENGTH: 18
<212> TYPE: DNA
<213> ORGANISM: Artificial Sequence
<220> FEATURE:

<223> OTHER INFORMATION: Synthetic Construct

<400> SEQUENCE: 55
acacgctaga gcagatac					18

<210> SEQ ID NO 56
<211> LENGTH: 19
<212> TYPE: DNA
<213> ORGANISM: Artificial Sequence
<220> FEATURE:
<223> OTHER INFORMATION: Synthetic Construct

<400> SEQUENCE: 56
gctggtataa ggtggtctc					19

<210> SEQ ID NO 57
<211> LENGTH: 20
<212> TYPE: DNA
<213> ORGANISM: Artificial Sequence
<220> FEATURE:
<223> OTHER INFORMATION: Synthetic Construct

<400> SEQUENCE: 57
gtgatcggtc ccaacaagga					20

<210> SEQ ID NO 58
<211> LENGTH: 20
<212> TYPE: DNA
<213> ORGANISM: Artificial Sequence
<220> FEATURE:
<223> OTHER INFORMATION: Synthetic Construct

<400> SEQUENCE: 58
gatgagaggg agcccatttg					20

<210> SEQ ID NO 59
<211> LENGTH: 19
<212> TYPE: DNA
<213> ORGANISM: Artificial Sequence
<220> FEATURE:
<223> OTHER INFORMATION: Synthetic Construct

<400> SEQUENCE: 59
gcctcgctaa gttacacag					19

<210> SEQ ID NO 60
<211> LENGTH: 18
<212> TYPE: DNA
<213> ORGANISM: Artificial Sequence
<220> FEATURE:
<223> OTHER INFORMATION: Synthetic Construct

<400> SEQUENCE: 60
agcaggtcag gttcacag					18

<210> SEQ ID NO 61
<211> LENGTH: 21
<212> TYPE: DNA
<213> ORGANISM: Artificial Sequence
<220> FEATURE:
<223> OTHER INFORMATION: Synthetic Construct

<400> SEQUENCE: 61
aagtggtgga tttggaagaa g					21

```
<210> SEQ ID NO 62
<211> LENGTH: 18
<212> TYPE: DNA
<213> ORGANISM: Artificial Sequence
<220> FEATURE:
<223> OTHER INFORMATION: Synthetic Construct

<400> SEQUENCE: 62
ccttggactc tgcctctg                                                    18
```